United States Patent
Voskoboynikov

(10) Patent No.: US 7,875,755 B2
(45) Date of Patent: Jan. 25, 2011

(54) CRACKING C5+ PARAFFINS TO INCREASE LIGHT OLEFIN PRODUCTION

(75) Inventor: Timur V. Voskoboynikov, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 658 days.

(21) Appl. No.: 11/949,014

(22) Filed: Nov. 30, 2007

(65) Prior Publication Data

US 2009/0143629 A1    Jun. 4, 2009

(51) Int. Cl.
*C07C 4/02* (2006.01)
*C07C 5/22* (2006.01)

(52) U.S. Cl. .................. 585/324; 585/648; 585/650; 585/752; 585/734

(58) Field of Classification Search ............. 585/324, 585/648, 650, 752, 734
See application file for complete search history.

(56) References Cited

U.S. PATENT DOCUMENTS

| | | | | |
|---|---|---|---|---|
| 5,254,781 | A | 10/1993 | Calamur et al. | 585/500 |
| 5,523,502 | A * | 6/1996 | Rubin | 585/324 |
| 5,599,510 | A | 2/1997 | Kaminsky et al. | 422/197 |
| 6,388,161 | B1 | 5/2002 | Dath et al. | 585/648 |
| 6,410,813 | B1 | 6/2002 | Dath et al. | 585/653 |
| 6,646,175 | B1 | 11/2003 | Dath et al. | 585/651 |
| 6,646,176 | B1 | 11/2003 | Dath et al. | 585/651 |
| 6,858,133 | B2 | 2/2005 | Dath et al. | 208/245 |
| 6,951,968 | B1 | 10/2005 | Dath et al. | 585/653 |
| 7,087,155 | B1 | 8/2006 | Dath et al. | 208/118 |

\* cited by examiner

*Primary Examiner*—Thuan Dinh Dang
(74) *Attorney, Agent, or Firm*—Arthur E Gooding

(57) ABSTRACT

A process for increasing the light olefin production from light paraffins is presented. The process includes separating paraffins from olefin streams and separately processing the paraffins.

16 Claims, No Drawings

CRACKING C5+ PARAFFINS TO INCREASE LIGHT OLEFIN PRODUCTION

BACKGROUND OF THE INVENTION

The present invention relates to a process for integrating the cracking of a paraffin rich stream with an olefin cracking process to increase the light olefin production of ethylene and propylene.

Ethylene and propylene, light olefin hydrocarbons with two or three atoms per molecule, respectively, are important chemicals for use in the production of other useful materials, such as polyethylene and polypropylene. Polyethylene and polypropylene are two of the most common plastics found in use today and have a wide variety of uses for both as a material fabrication and as a material for packaging. Other uses for ethylene and propylene include the production of vinyl chloride, ethylene oxide, ethylbenzene and alcohol. The production of light olefins is predominantly performed through steam cracking, or pyrolysis, of larger hydrocarbons. Hydrocarbons used as feed stock for light olefin production include natural gas, petroleum liquids, and carbonaceous materials including coal, recycled plastics or any organic material.

Methods are known for increasing the conversion of portions of the products of the ethylene production from a zeolitic cracking process to produce more ethylene and propylene by a disproportionation or metathesis of olefins. Such processes are disclosed in U.S. Pat. Nos. 5,026,935 and 5,026,936 wherein a metathesis reaction step is employed in combination with a catalytic cracking step to produce more ethylene and propylene by the metathesis of $C_4$ and heavier molecules. The catalytic cracking step employs a zeolitic catalyst to convert a hydrocarbon stream having 4 or more carbon atoms per molecule to produce olefins having fewer carbon atoms per molecule. The hydrocarbon feedstream to the zeolitic catalyst typically contains a mixture of 40 to 95 wt-% paraffins having 4 or more carbon atoms per molecule and 5 to 60 wt-% olefins having 4 or more carbon atoms per molecule. In U.S. Pat. No. 5,043,522, it is disclosed that the preferred catalyst for such a zeolitic cracking process is an acid zeolite, examples includes several of the ZSM-type zeolites or the borosilicates. Of the ZSM-type zeolites, ZSM-5 was preferred. It was disclosed that other zeolites containing materials which could be used in the cracking process to produce ethylene and propylene included zeolite A, zeolite X, zeolite Y, zeolite ZK-5, zeolite ZK-4, synthetic mordenite, dealuminized mordenite, as well as naturally occurring zeolites including chabazite, faujasite, mordenite, and the like. Zeolites which were ion-exchanged to replace alkali metal present in the zeolite were preferred. Preferred cation exchange cations were hydrogen, ammonium, rare earth metals and mixtures thereof.

European Patent No. 109,059B1 discloses a process for the conversion of a feedstream containing olefins having 4 to 12 carbon atoms per molecule into propylene by contacting the feedstream with a ZSM-5 or a ZSM-11 zeolite having a silica to alumina atomic ratio less than or equal to 300 at a temperature from 400 to 600° C. The ZSM-5 or ZSM-11 zeolite is exchanged with a hydrogen or an ammonium cation. The reference also discloses that, although the conversion to propylene is enhanced by the recycle of any olefins with less than 4 carbon atoms per molecule, paraffins which do not react tend to build up in the recycle stream. The reference provides an additional oligomerization step wherein the olefins having 4 carbon atoms are oligomerized to facilitate the removal of paraffins such as butane and particularly isobutane which are difficult to separate from $C_4$ olefins by conventional fractionation. In a related European Patent 109060B1, a process is disclosed for the conversion of butenes to propylene. The process comprises contacting butenes with a zeolitic compound selected from the group consisting of silicalites, boralites, chromosilicates and those zeolites ZSM-5 and ZSM-11 in which the mole ratio of silica to alumina is greater than or equal to 350. The conversion is carried out at a temperature from 500 to 600° C. and at a space velocity of from 5 to 200 kg/hr of butenes per kg of pure zeolitic compound. The European Patent 109060B1 discloses the use of silicalite-1 in an ion-exchanged, impregnated, or co-precipitated form with a modifying element selected from the group consisting of chromium, magnesium, calcium, strontium and barium.

Improvements and integration with other processes can improve yields of light olefins by increasing the utilization of other process streams. Also, improving the use of processes that yield intermediate process streams which can be diverted for conversion to light olefins can result in significant yield increases.

BRIEF SUMMARY OF THE INVENTION

The present invention comprises generating light olefins, comprising ethylene and propylene, from paraffins in the C4+ range, preferably in the C4 to C6 range, and more preferably C5 and C6 paraffins. The process comprises passing an olefin rich stream to a first olefin cracking reactor. The olefin cracking reactor cracks light olefins from heavier olefins and generates a process stream comprising light olefins and paraffins. The process stream is separated into a first stream rich in the light olefins, a second stream comprising butenes and butanes, and a third stream comprising un-converted paraffins. The butene rich second stream is recycled and passed to the olefin cracking reactor to generate more light olefins. The paraffin rich third stream comprises paraffins in the C5+ range and is passed to a paraffin cracking reactor for the generation of light olefins in the paraffin process stream. The paraffins are more difficult to crack than olefins, and it has been found that in the presence of olefins these paraffins crack much less than in their absence, over catalysts that are used for cracking olefins.

Other objects, advantages and applications of the present invention will become apparent to those skilled in the art from the following detailed description.

DETAILED DESCRIPTION OF THE INVENTION

The production of olefins by cracking is known, and there are many technologies for cracking large hydrocarbons. However, smaller hydrocarbons are more difficult to crack, therefore they are often used for other purposes, such as leaving pentanes in naphtha feedstocks for use in gasoline, or using n-pentane as a desorbent in simulated moving bed separation processes. In addition, cracking of large hydrocarbon molecules results in intermediate streams that are further processed downstream, and can include separate more specialized cracking processes. While cracking of paraffins is known, and paraffin conversion to olefins is known to strongly depend on temperature and WHSV. Operating a reactor to crack olefins at temperatures greater than 600° C. and at WHSV less than 6 $hr^{-1}$ generates higher yields of light olefins. The term light olefins as used hereinafter refers to ethylene and propylene. However, these operating conditions result in faster deactivation of catalyst. This results in more frequent regenerations, which are expensive, and shorter overall life of the catalyst before a reload is required.

The olefin cracking process was developed to crack large olefin molecules to produce light olefins because of the greater economic value of light olefins. In the olefin cracking process, there is a build up of paraffins in the recycle loop. Cracking the paraffins=increases the light olefin yield and prevents paraffin build up. The process of the present invention comprises a method to increase the light olefin yield from the uncracked paraffins.

It was unexpected, but found that when olefins were removed from a process stream, the cracking of paraffins improved such that the amount of olefins in the product stream did not decrease. Without being bound to any theory, it is believed that the presence of olefins contributes to a suppression of the cracking of paraffins. It was also found that the cracking of isoparaffins generated a greater propylene yield over the cracking of normal paraffins. The cracking of isoparaffins, specifically isopentane, will generate more ethylene and propylene, whereas, the cracking of n-paraffins will, in general, generate light olefins and more of un-converted paraffin that requires recycling or other further processing.

The present invention provides for the production of the light olefins of ethylene and propylene from the build-up of paraffins in the C4+ range resulting from the olefin cracking process. The process comprises passing an olefin rich stream to a first olefin cracking unit operated at olefin cracking conditions, thereby generating an olefin process stream. The olefin process stream is separated in a separation unit to generate a product, or first, stream rich in ethylene and propylene, a second stream comprising butanes and butenes, and a third stream comprising unconverted paraffins. The second stream is recycled to the olefin cracking unit for further cracking of the butenes, and the third stream is passed to a paraffin cracking unit operated at paraffin cracking reaction conditions.

The olefin reaction cracking conditions include a temperature between 500° C. to 650° C., and preferable between 550° C. to 580° C. The olefin cracking conditions are operated at relatively low pressures between 100 kPa (14.5 psia) and 200 kPa (29 psia), and preferably between 120 kPa (17.4 psia) and 160 kPa (23.2 psia). The weight hourly space velocity (WHSV) for the olefin cracking unit is between 8 and 16 $hr^{-1}$.

The paraffin reaction cracking conditions include a temperature between 550° C. to 700° C., and preferable between 580° C. to 620° C. The paraffin cracking conditions are operated at relatively low pressures between 100 kPa (14.5 psia) and 200 kPa (29 psia), and preferably between 120 kPa (17.4 psia) and 160 kPa (23.2 psia). The weight hourly space velocity (WHSV) for the olefin cracking unit is between 4 and 8 $hr^{-1}$. In a preferred operation, the paraffin cracking uses a silicalite catalyst that has been steamed and acid washed. The silicalite catalyst preferably has a silica to alumina ratio from 300 to 500. The paraffin cracking catalyst can be an olefin cracking catalyst. It was found that the olefin cracking catalyst works well for cracking paraffins in the absence of olefins, but that the conditions for cracking need to be altered for paraffin cracking conditions.

In another embodiment, the process further comprises the use of a second olefin cracking unit, wherein the second stream is passed to the olefin cracking unit instead of recycling the second stream to the first olefin cracking unit. The second olefin cracking unit is operated at the same low pressures or lower pressures than the first olefin cracking unit.

It is believed that isoparaffins are more easily cracked than normal paraffins. In another embodiment, the process comprises passing the third stream to an isomerization reactor, thereby generating a fourth stream having normal and iso-paraffins. The fourth stream is passed to the paraffin cracking unit, thereby generating a product stream comprising light olefins.

The product stream is passed to a separation unit to separate light olefins from the product stream and to create a recycle stream for returning paraffins to the paraffin cracking reactor.

EXPERIMENTAL

It was believed that the presence of small amounts of olefins facilitated the cracking of paraffins. However, research has indicated this idea is not true and that the paraffins will crack without the olefins present, over a catalyst usually used for olefin cracking. The process for cracking paraffins in the C4+ range can be performed by passing the paraffins to a separate reactor at similar operating conditions, but at elevated temperatures relative to the olefin cracking units.

Experiments were performed to study the cracking of normal and iso-paraffins, and to compare the generation of light olefins. By separating the paraffins from olefins, a substantial increase in light olefin production can be realized. The feed for the base case, and the high temperature case comprised a mixture of approximately 40 wt % C4 olefins and 60 wt % C4 paraffins. The feed for the paraffins case comprised approximately 95 wt % C5 paraffins and 5 wt % C5 olefins.

TABLE

Results of olefin production

| | WHSV | T, °C. | C2= | C3= | C4= | C5= | C4 | C5 |
|---|---|---|---|---|---|---|---|---|
| Base case | 13.5 | 568 | 4.2 | 15.2 | 13.9 | 3.3 | 57.3 | 0.3 |
| High T case | 6.7 | 597.5 | 5.5 | 17.3 | 17.5 | 1.8 | 51.1 | 0.4 |
| isoparaffins | 6.7 | 593 | 8.0 | 15.0 | 10.4 | 3.25 | 1.6 | 48.3 |
| n-paraffins | 6.7 | 600 | 4.6 | 12.8 | 6.1 | 1.9 | 1.0 | 49.3 |

The results indicate that cracking of a C5 paraffin stream without olefins can yield significant amounts of the light olefins ethylene and propylene. Since the cracking of a paraffin stream comprising isoparaffins and n-paraffins, and n-pentane is much less reactive than isopentane, and a stream comprising isopentane and n-pentane will preferentially crack the isopentane, thereby resulting in an intermediate stream relatively rich in n-pentane. By recycling the n-pentane stream through an isomerization reactor before directing the n-pentane stream back to the cracking reactor, the light olefin yields are increased.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for increasing the light olefin yields from an olefin cracking process, comprising:

passing an olefin rich stream to a first olefin cracking unit operated at olefin cracking reaction conditions, thereby generating an olefin process stream;

passing the olefin process stream to a separation unit thereby generating a first stream rich in propylene and ethylene, a second stream comprising butenes and butanes, and a third stream comprising un-converted paraffins;

passing the second stream to a second olefin cracking unit, and the second olefin cracking unit is operated at a lower pressure than the first olefin cracking unit;

passing the third stream to an isomerization reactor to generate a fourth stream comprising normal and iso-paraffins; and passing the fourth stream to a paraffin cracking unit operated at paraffin cracking reaction conditions, thereby generating a paraffin process stream.

2. The process of claim 1 wherein the first olefin cracking unit is operated at a temperature from 500° C. to 650° C.

3. The process of claim 2 wherein the first olefin cracking unit is operated at a temperature from 550° C. to 580° C.

4. The process of claim 1 wherein the first olefin cracking unit is operated at a pressure between 100 kPa (14.5 psia) and 200 kPa (29 psia).

5. The process of claim 4 wherein the first olefin cracking unit is operated at a pressure between 120 kPa (17.4 psia) and 160 kPa (23.2 psia).

6. The process of claim 1 wherein the first olefin cracking unit is operated at a weight hourly space velocity between 8 and 16 $hr^{-1}$.

7. The process of claim 1 wherein the paraffin cracking unit is operated at a temperature from 550° C. to 700° C.

8. The process of claim 7 wherein the paraffin cracking unit is operated at a temperature from 580° C. to 620° C.

9. The process of claim 1 wherein the paraffin cracking unit is operated at a pressure between 100 kPa and 200 kPa.

10. The process of claim 1 wherein the paraffin cracking unit is operated at a pressure between 120 kPa and 160 kPa.

11. The process of claim 1 wherein the paraffin cracking unit is operated at a weight hourly space velocity between 4 and 8 $hr^{-1}$.

12. The process of claim 1 further comprising passing the paraffin process stream to the separation unit.

13. The process of claim 1 wherein the paraffin cracking unit has a silicalite catalyst.

14. The process of claim 13 wherein the catalyst has a silica to alumina ratio from 300 to 500.

15. The process of claim 13 wherein the catalyst is steamed and acid washed.

16. The process of claim 1 wherein the paraffins and olefins are in the C4 to C6 range.

* * * * *